(12) United States Patent
Sibbett et al.

(10) Patent No.: US 7,402,229 B2
(45) Date of Patent: Jul. 22, 2008

(54) FABRICATION AND USE OF SEMIPERMEABLE MEMBRANES AND GELS FOR THE CONTROL OF ELECTROLYSIS IN A MICROFLUIDIC DEVICE

(75) Inventors: Scott Sibbett, Corrales, NM (US); Dimiter Petsev, Albuquerque, NM (US)

(73) Assignees: Intel Corporation, Santa Clara, CA (US); University of New Mexico, Albuquerque, NM (US)

( * ) Notice: Subject to any disclaimer, the term of this patent is extended or adjusted under 35 U.S.C. 154(b) by 23 days.

(21) Appl. No.: 10/815,346

(22) Filed: Mar. 31, 2004

(65) Prior Publication Data
US 2005/0217990 A1    Oct. 6, 2005

(51) Int. Cl.
*G01N 27/453* (2006.01)
*B01L 11/00* (2006.01)

(52) U.S. Cl. .................. 204/601; 204/606; 204/605; 422/101

(58) Field of Classification Search .......... 204/450; 264/166; 249/145
See application file for complete search history.

(56) References Cited

U.S. PATENT DOCUMENTS

| | | | |
|---|---|---|---|
| 6,514,767 B1 | 2/2003 | Natan | |
| 6,554,985 B2* | 4/2003 | Ruiz-Martinez et al. | 204/451 |
| 6,685,809 B1* | 2/2004 | Jacobson et al. | 204/450 |
| 6,942,773 B1* | 9/2005 | Olivares et al. | 204/452 |
| 2003/0136679 A1* | 7/2003 | Bohn et al. | 204/543 |
| 2005/0061714 A1 | 3/2005 | Sibbett et al. | |

OTHER PUBLICATIONS

Page 48 of bioanalytical chemistry by Manz et al., Imperial College Press, 2004.*
Temperature Classes of Electrical Insulators by Shimizu Ohta, Three Bond Technical News, issued Dec. 1, 1985.*
Mulvaney et al., "Glass-Coated, Analyte- Tagged Nanoparticles: A New Tagging System Based On Detection With Surface-Enhanced Raman Scattering", Langmuir, 2003, vol. 19, pp. 4784-7490.
Doering et al., "Spectroscopic Tags Using Dye-Embedded Nanoparticles and Surface-Enhanced Raman Scattering", Analytical Chemistry, pp. A-F.

* cited by examiner

*Primary Examiner*—Alex Noguerola
(74) *Attorney, Agent, or Firm*—Darby & Darby PC (57) ABSTRACT

A microfluidic device and method is disclosed having one or more membranes for the control of electrolysis. In one embodiment, a microfluidic device is disclosed that includes body with first channel and second channels separated by a gel layer. A first electrode positioned in the first channel and a second electrode positioned in the second channel wherein a potential applied to the first and second electrodes passes electrons from the first channel to the second channel through the gel layer. In another embodiment, a microfluidic device includes a body having a surface with a channel separating two first reservoirs. One or more membranes are positioned on the surface covering a portion of the channel and a blank is positioned covering the channel and the one or more membranes. A second reservoir through the blank is in contact with the membrane, each second reservoir in communication with the channel via the membrane. A first electrode is positioned in the first reservoir and a second electrode is positioned in the second reservoir wherein a potential applied to the first and second electrodes passes electrons from the first channel to the second channel through the membranes.

10 Claims, 7 Drawing Sheets

FABRICATION AND USE OF SEMIPERMEABLE MEMBRANES AND GELS FOR THE CONTROL OF ELECTROLYSIS IN A MICROFLUIDIC DEVICE

FIELD OF THE INVENTION

This invention relates generally to an apparatus and method of fabricating microfluidic chips for segregating electrolysis products from analyte and electrochromagrphic separation.

BACKGROUND OF THE INVENTION

Several methods have been employed of segregating electrolysis products from analyte. On method employs (i) inserting electrodes into open reservoirs for maximum release of the gaseous products from electrolysis (dihydrogen and dioxygen). Another method employs reservoirs in sufficient volume that the ionic products of electrolysis (protons and hydroxide ion) do not overwhelm the buffering capacity of the buffer solution in the reservoir. However, these methods do not address the issues pertaining to the ionic products of electrolysis.

Techniques such as electrophoresis and chromatography may be used to separate charged molecules such as deoxyribonucleic acid (DNA), ribonucleic acid (RNA) and proteins. Generally, electrophoresis is used to separate charged molecules on the basis of their movement in an electric field. Chromatography on the other hand, is used to separate molecules based on their distribution between a stationary phase and a mobile phase.

Polyacrylamide gel electrophoresis (PAGE) is a standard tool in the study of proteins. Generally, with PAGE, proteins and peptides are exposed to a denaturing detergent such as sodium dodecylsulfate (SDS). SDS binds proteins and peptides. As a result, the proteins/peptides unfold and take on a net negative charge. The negative charge of a given SDS treated protein/peptide is roughly proportional to its mass. An electric field is then applied which causes the negatively charged molecules to migrate through a molecular sieve created by the acrylamide gel. Smaller proteins or peptides migrate through the sieve relatively quickly whereas the largest proteins or peptides are the last to migrate, if at all. Those molecules having a mass between the two extremes will migrate in the gel according to their molecular weight. In this way, proteins that differ in mass by as little as 2% may be distinguished.

Polyacrylamide gel electrophoresis may be used in conjunction with other electrophoretic techniques for additional separation and characterization of proteins. For example, native proteins may be separated electrophoretically on the basis of net intrinsic charge. That is, the intrinsic charge of a protein changes with the pH of the surrounding solution. Thus, for a given protein there is a pH at which it has no net charge. At that pH, the peptide will not migrate in an electric field. Thus, when proteins in a mixture are electrophoresed in a pH gradient, each protein will migrate in the electric field until it reaches the pH at which its net charge is zero. This method of protein separation is known as isoelectric focusing (IEF).

Isoelectric focusing and SDS-PAGE are commonly used in sequence to separate a protein or peptide mixture first in one dimension by IEF and then in a second dimension by PAGE. Isoelectric focusing followed by SDS-PAGE is commonly referred to as 2D-PAGE. Disadvantageously, 2D-PAGE requires the use of bulky equipment. Further, the chemicals required to run 2D-PAGE separations can be expensive and potentially hazardous. Additionally, running 2D-gels can be time consuming and usually requires a skilled technician to obtain satisfactory results. Even then, results may be variable and difficult to reproduce.

Other separation techniques, such as Matrix Assisted Laser Desorption/Ionization Time-Of-Flight Mass Spectrometry (MALDI-TOFMS) are available to separate polar compounds including proteins. However, MALDI-TOFMS requires a substantial investment in expensive equipment and labor, and does not improve upon the core 2D-PAGE separation technology.

Thus, there is a need for improved devices for (i) mitigating the gaseous and ionic products of electrolysis, particularly with regard to microfluidic devices; (ii) a media for electrochromatographic sieving of charged molecules which is easily fabricated and which offers significantly improved performance over conventional sieving media; (iii) a robust, reliable and easily fabricated filter which prevents ambient particles from entering fluidic channels, particularly microfluidic and nanofluidic channels; and (iv) a robust fluidic element which is able to buffer hydraulic pressure surges.

BRIEF DESCRIPTION OF THE DRAWINGS

In the following detailed description of the invention reference is made to the accompanying drawings which form a part hereof, and in which are shown, by way of illustration, specific embodiments in which the invention may be practiced. These embodiments are described in sufficient detail to enable those skilled in the art to practice the invention. Other embodiments may be utilized, and structural, logical, and electrical changes may be made, without departing from the scope of the present invention.

DETAILED DESCRIPTION OF THE INVENTION

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials. similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The description of some of the embodiments of the invention given below refers to a microfluidic device built from polymethylsiloxane material (PDMS). However, there are no known constraints to adapting the essence of the fabrication protocol described here for the fabrication of devices built of other materials, such as glass, silicon, plastic, etc. Also, although the invention described below refers to a simple microfluidic system, there is no known constraint upon either the scale of the device (e.g., macroscale versus microscale versus nanoscale), or upon the complexity of the network of channels (single channels versus branched channels versus serial channels versus channels of greater even complexity).

Figure 1:
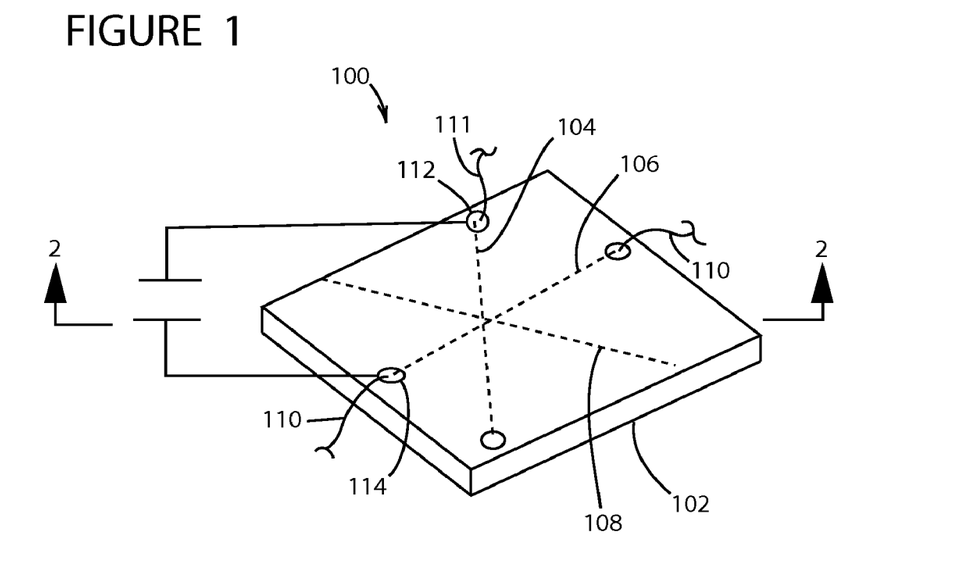
FIG. 1 is a perspective view showing one embodiment of a microfluidic device.
Figure 2:
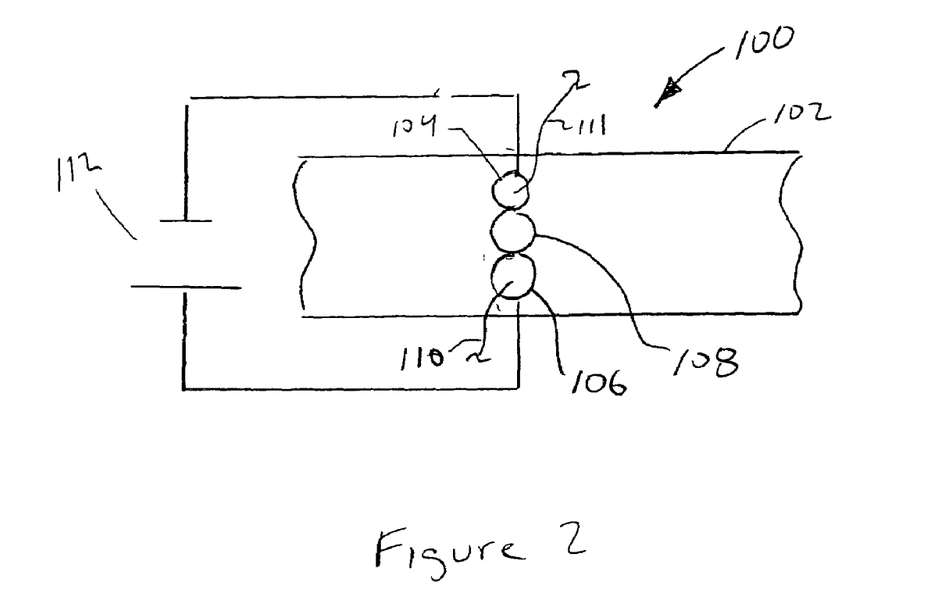
FIG. 2 is a cross sectional view of FIG. 1 taken at 2-2.

FIGS. 1 and 2 are perspective and cross-sectional views showing one embodiment of a microfluidic device 100 that utilizes a gel membrane to control electrolysis. The device 100 includes a body 102 having a 3-level structure with an upper channel 104 and a lower channel 106 separated by a gel plug, layer or membrane 108. In use, the upper channel 104 is filled with buffer and analyte solution and the lower channel 106 is filled with an electrolyte solution separated by the gel membrane 108. Electrodes 110 and 111 are placed in contact with the solutions in the upper 104 and lower 106 channels, preferably at reservoirs 112 and 114. A potential is applied to the electrodes. By placing a ground electrode 111 in one of the reservoirs 112 of the upper channel 104, charged molecules in the lower channel 106 will pass through the gel membrane 108 into the upper channel 104, leaving behind any electrolysis products which are created at the electrode surface.

FIGS. 2-6 show one method of fabricating a microfluidic device or chip, such as the microfluidic device 100 shown in FIG. 1, for the purpose of segregating electrolysis products from analyte. In one embodiment, the microfluidic device or chip uses polymethylsiloxane material (PDMS) for the body 102 and agarose material for the gel membrane 108.

Figure 3:
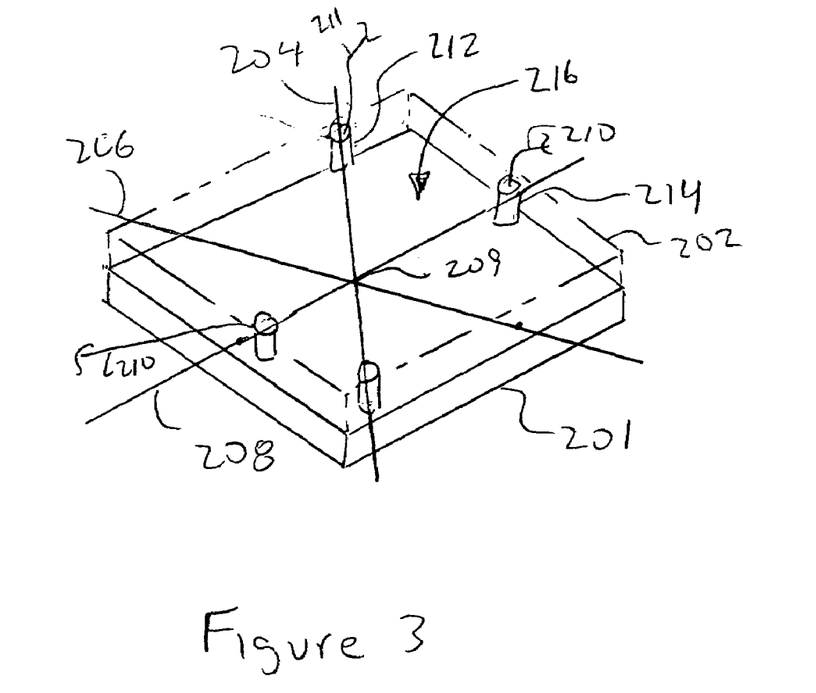
FIGS. 3-6 are perspective views showing one method of fabrication of a microfluidic device.

Referring now to FIG. 3, three wires 204, 206, 208 are placed atop each other on a substrate 201, such as glass or silicon, and secured via tape, glue or other suitable means. The wires include an upper wire 204, a middle wire 206 and a lower wire 208. The three wires are in contact at a midpoint or point 209 and may be positioned in any orientation. In the figures, the wires are positioned radially at 0°, 120° and 240° degrees from the point 209. Reservoir posts 212 are positioned near the upper wire 204 and reservoir posts 214 are positioned near the lower wire 206 spanning the point 209. Electrodes 210, 211 may be introduced at this point, as desired. Walls or other containment systems (not shown) are positioned around the components during fabrication to contain a mold material. The mold material, such as uncured PDMS 216, is poured over the substrate 201, wires 204, 206, 208 and reservoir posts 212, 214. The PDMS 216 is cured forming a replica 202, which is then peeled from the substrate 201. The reservoir posts 212 are pulled out of the replica 202 forming reservoirs 213, and the reservoir posts 214 are pulled out of the replica 202 forming reservoirs 215.

Figure 4:
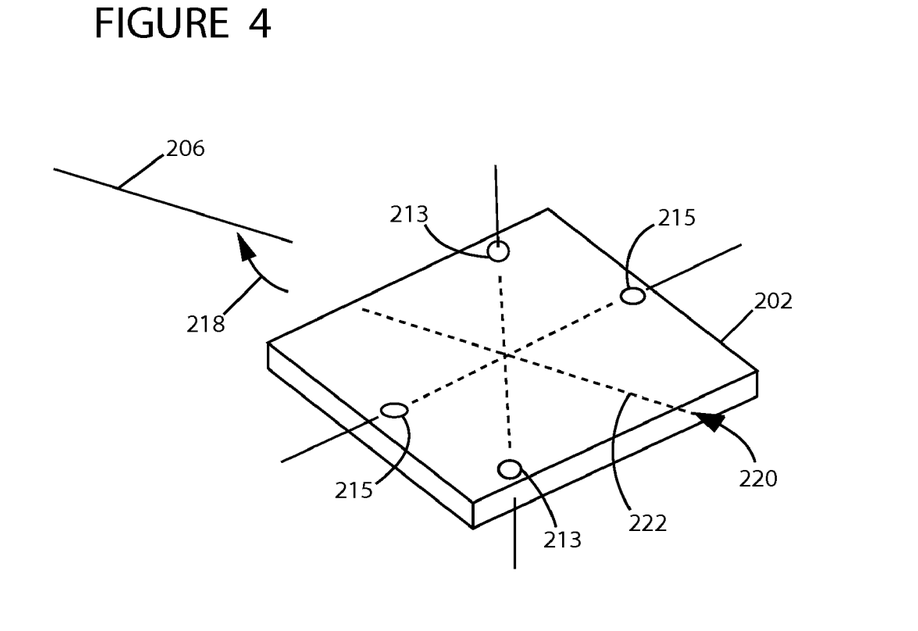
Figure 5:
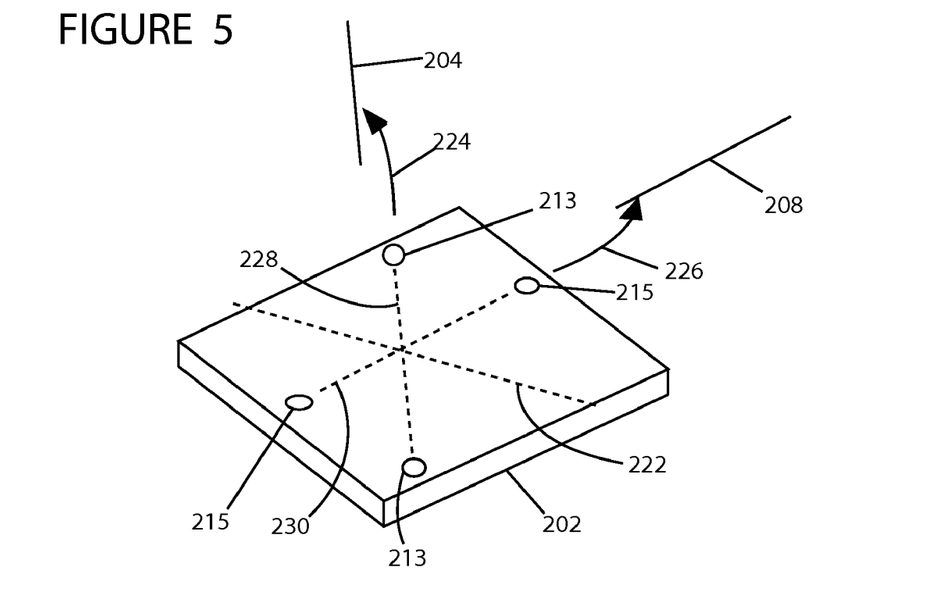

FIG. 4 shows the middle wire 206 of the stack of three being extracted 218 from the body 202, leaving behind a single open channel into which unpolymerized gel, such as agarose, is inserted 220. Upon curing, the agarose forms a gel plug, layer or membrane 222. In FIG. 5, the upper wire 204 is extracted 224 from the body 202, leaving behind an upper channel 228 in communication with reservoir ends 213 and the gel membrane 222, and the lower wire 208 is extracted 226 from the body 202, leaving behind a lower channel 230 in communication with reservoir ends 215 and the gel membrane 222. The upper channel 228 and the lower channel 230 are in communication with each other only via the intervening gel membrane 222.

Figure 6:
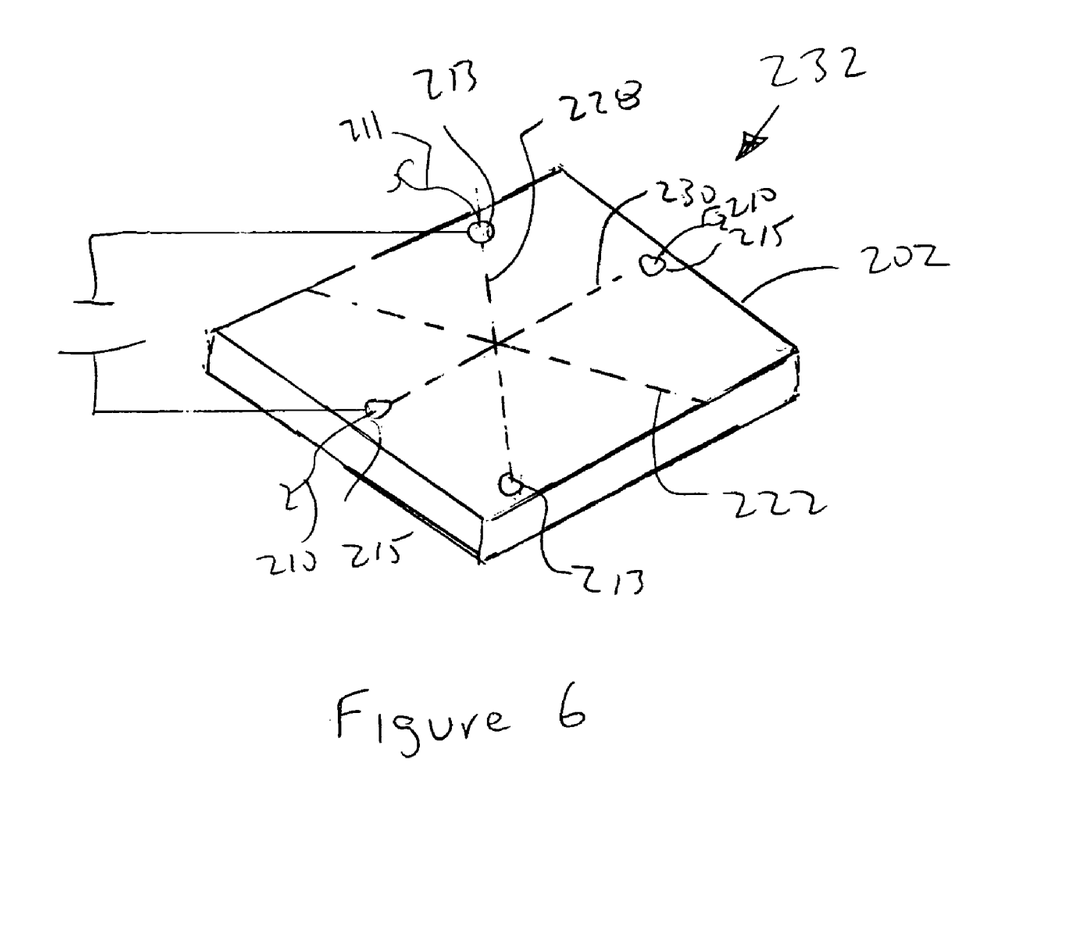

A finished microfluidic device 232 is shown in FIG. 6. In use, the upper channel 228 is filled with buffer and analyte, and the lower channel 230 is filled with electrolyte. Electrodes 210 are in contact with the electrolyte in the lower channel, preferably at reservoirs 215, and potentials applied to the electrodes. The electrodes may receive voltage from any suitable power supply. A ground electrode 211 is placed in one of the reservoirs 213 of the upper channel 228. In use, the electrons introduced into the lower channel 230 migrate through the gel 206 and impose a potential in the upper channel 228. However, the products of electrolysis do not pass through the gel membrane 206 in appreciable amounts, hence they remain in the lower channel 230 and segregated from the analyte in the upper channel 228. This establishes a field within the upper electrode which is free of electrolysis products. The microfluidic device permits the application of electric potential to PDMS microfluidic in-channel electrodes without perturbing the pH of the buffer, or perturbing the fluid dynamics of the system via bubble generation. Other embodiments of the invention envision various semi-permeable membranes, and other configurations of the channels and electrodes.

Figure 7:
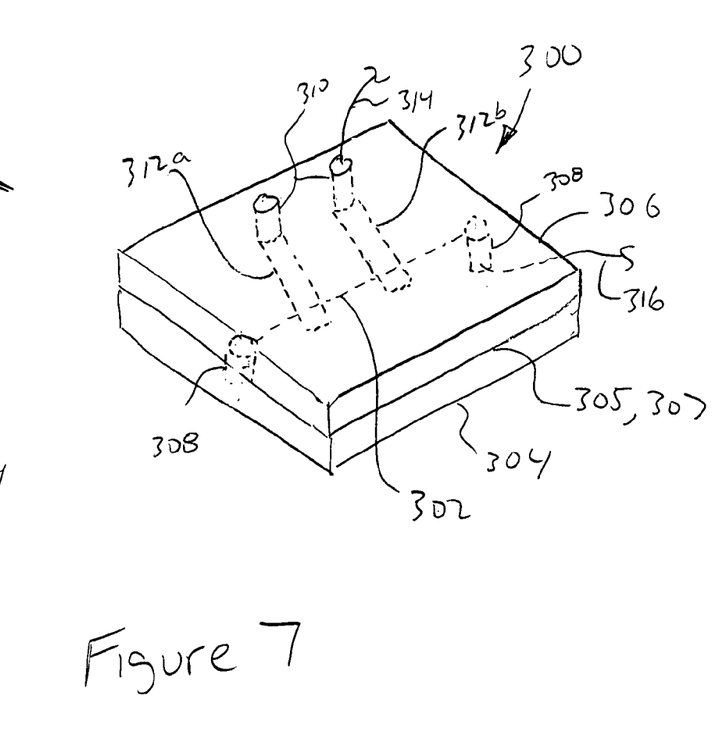
FIG. 7 shows another embodiment of a microfluidic device.

FIG. 7 shows fabrication of another embodiment of a microfluidic device 300 utilizing a semipermeable membrane. First, a PDMS replica 304 containing a channel 302 is fabricated by conventional soft lithography, with or without integral silicone take-offs (bottom left of FIG. 7). A blank 306 is also fabricated. Macroscale reservoirs 308 may be cored in the replica 304 connecting the channel 302. Additional reservoirs 310 may be cored in the blank 306, at suitable locations some distance from the channel 302. One or more semi-permeable membranes 312, such as regenerated cellulose, may be placed upon a surface 307 of the blank 306 (upper left of FIG. 7). Optionally, the membranes 312 may be place upon a surface 305 of the replica 302 covering a portion of the channel 302. When the replica 304 and blank 306 are joined, the two surfaces 305 and 307 are mated. The membrane 312 overlaps a portion of the channel 302 near one end and is connected to a reservoir 310 near another end (right side of FIG. 7).

In another embodiment, prior to mating, the surfaces 305 and 307 may be exposed to a conventional oxygen plasma, and allowed to sit undisturbed for at least 30 minutes. In another embodiment, prior to mating, the membrane 312 can be covered with a curable glue in such a manner as to leave bare membrane 312 exposed in the well of the reservoir 310 and in the channel 302. In another embodiment, the resulting device 300 may be clamped between two flat surfaces (not shown). Macroscale tubing may then connected to the silicone takeoffs, if present.

In use, the reservoirs 308, 310 and/or other fluidic ports are filled with one or more liquids which come into contact with the membranes 312. The resulting liquid filled device is allowed to sit long enough to permit diffusion of liquid through the membranes 312, from reservoir 310 to channel 302 (or vice versa). Optionally, before or after the wetting of the membrane 312, the reservoir 310 or channel 302 is filled with liquids, therefore completing fluidic contact between reservoir 310 and channel 302 via the wetted membrane 312. Finally, a ground electrode 314 is inserted in one of the macroscale reservoirs 310, and a powered electrode 316 is inserted into at least one other reservoir 308.

The microfluidic device 300 may be operated as follows. Fluid is added to the one or more reservoirs 308, 310. Voltage is applied to the electrodes 314, 316 to cause current to pass through the membrane 312 and into the channel 302. Many different voltages may be applied to the microfluidic device 300. It has been observed that if more than about 1.4 volts is applied between the electrodes, then the products of electrolysis will evolve from the electrodes in the reservoirs. The gaseous products of electrolysis will release as bubbles to the ambient air, whereas the ionic products of electrolysis will tend to be buffered by the macroscale volume of buffer in the reservoirs. Due to the extremely low rate of diffusive and convective flow in the plane of the semipermeable membrane 312, the ionic products will tend to be sequestered from the channel 302. Tests have been conducted that successfully furnished up to 1000V to microscale PDMS~120 micron diameter channels without interference from electrolysis. Above 1000V, ohmic heating of solution in the channel may tend to interfere with the performance of a microfluidic device. With more thermally-conductive substrates and/or chips with channels of smaller cross-section, higher voltages are probably attainable.

The reservoirs and solutions are a point of entry of particles into micro- and nano-scale channels of typical devices. However, in the microfluidic device 300 described herein, the membrane 312 completely blocks all such particles from entering the channel 302. Moreover, since the membrane 312 is positioned between both the channel 302 and the reservoir 310, there is no intermediate tubing or channels within which particles can become stuck. Semipermeable membranes are often sold according to their molecular weight cutoff (MWCO). By selecting a membrane of a certain MWCO, it is possible to control which charged molecules can or cannot be electrically-driven into the membrane for subsequent electrochromatographic sieving. Indeed, two or more membranes of differing MWCOs could be employed in a single device, such as membranes 312a and 312b shown in FIG. 7, to provide for fractionating a complex mixture, first according to MWCO, and then via electrochromatography in the plane of the membrane.

Figure 8:
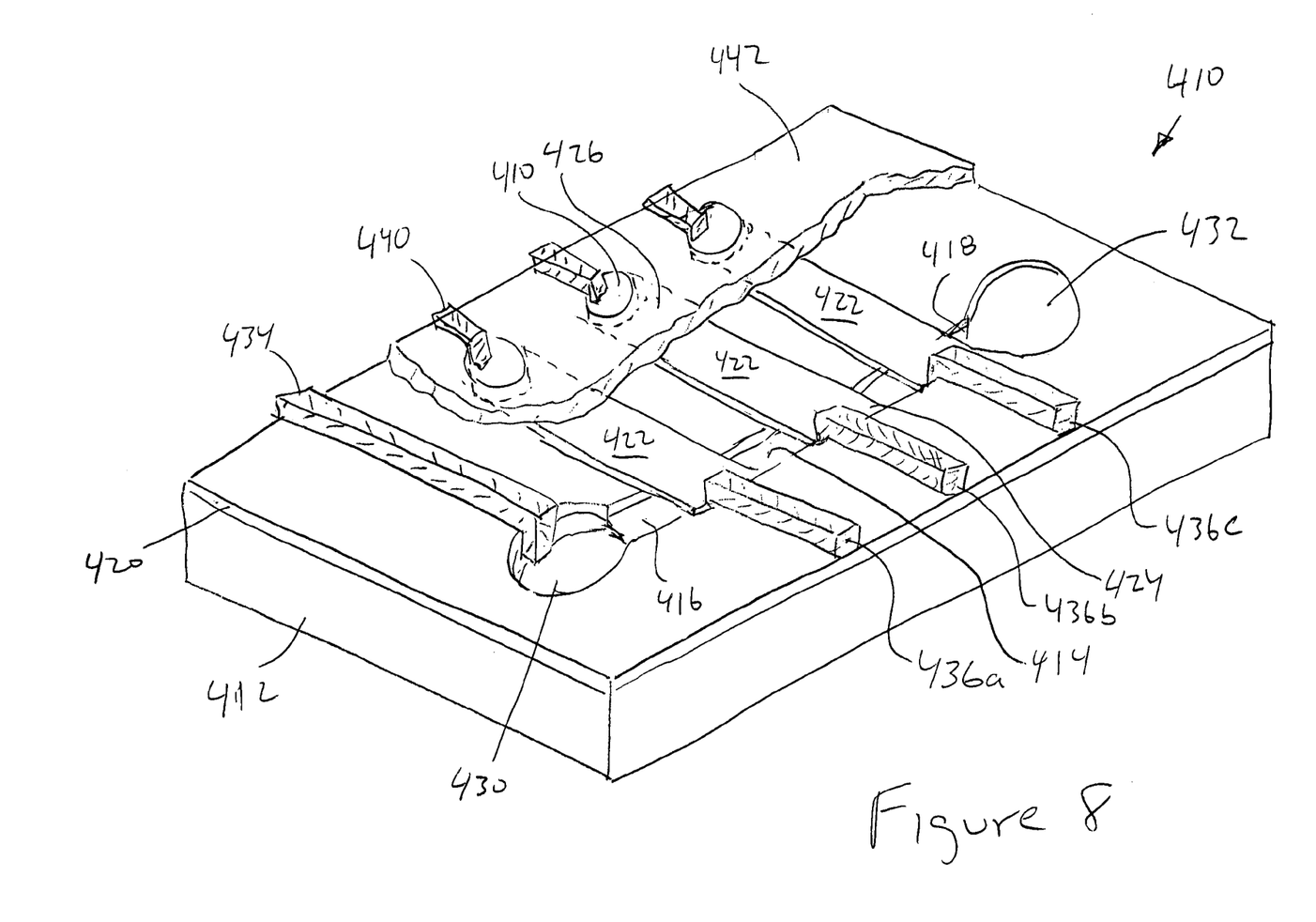
FIG. 8 shows another embodiment of a microfluidic device.

FIG. 8 shows one embodiment of a multi-step-separation microfluidic device 410 using one or more of the membrane disclosed above. Many of the details of a multi-step-separation device are disclosed in U.S. patent application Ser. No. 10/666,116, titled SORTING CHARGED PARTICLES, filed Sep. 18, 2003, the contents of which are incorporated by reference. In the multi-step-separation microfluidic device, electric fields of different strength are established within discrete segments of a microfluidic channel or network, which in turn establish counteracting electrophoretic, electroosmotic and/or hydrodynamic forces, and by which charged molecules can be made to focus at discrete points within the channel, followed by a second dimension sort based on molecular sieving.

For the purposes of the following discussion, the term "node" means a point along a channel where a membrane intersects a channel. By fabricating two or more nodes along a given channel, it is possible to perform field gradient focusing as a first step in a two-step separation process. Three nodes are shown in FIG. 8. Once charged molecules or families of charged molecules are focused at specific nodes, a different orientation of the electric field can be applied which drives the focused molecules into a membrane. The membrane may be a gel or a semipermeable membrane of MWCO which permits entry of the focused molecules, followed by molecular sieving in the plane of the membrane.

The microfluidic device 410 may be constructed according to known macro and micro scale fabrication techniques. For example, in embodiments where the microfluidic device 410 is to be fabricated on the microscale, such as with Micro-Electro-Mechanical System (MEMS), complementary metal oxide silicon (CMOS) or other known semiconductor processing techniques may be utilized to form various features in and on a substrate 412. With MEMS, electronic and micro-mechanical components may reside on a common substrate. Thus, according to some embodiments of the present invention, the microfluidic device 410 may have circuits and MEMS components formed thereon. Further, according to some embodiments of the present invention, MEMS components may include but are not limited to microfluidic channels, reservoirs, electrodes, detectors and/or pumps.

The substrate 412 may be any material, object or portion thereof capable of supporting the device 410. For example, in some embodiments of the present invention, the substrate 412 may be polymethylsiloxane material (PDMS). Alternately, the substrate 412 may be any other material suitable for forming microfluidic channels therein as such semiconductor material such as silicon with or without additional layers of materials deposited thereon, glass, quartz, silica, polycarbonate or dichlorodimethylsilane (DDMS). Advantageously, biocompatible materials such as parylene may be utilized to coat channels or other surfaces thereby minimizing absorption of charged molecules. If parylene is not utilized in a particular embodiment, the substrate 412 may be otherwise treated to minimize reaction between the substrate 412 and the particles to be sorted.

FIG. 8 shows the fabrication of one embodiment of the device 400. A channel 414 is formed in the substrate 412, for example by etching according to known techniques, and may be of any desired length, width, depth and shape. According to some embodiments of the present invention, the channel 414 may be elongate having two ends 416 and 418 extending toward opposing ends of the substrate 412, although the invention is not so limited. Further, in embodiments where the channel 414 is a microfluidic channel, its width, depth and perhaps length may range from a few micrometers to a millimeter or more in dimension.

One or more membranes 422 may be placed on the substrate 412, overlapping the channel 414, such as described above. The membranes 422 are coupled to the channel 414 such that they have one end 424 overlapping the channel 414 and a second end 426 remote from channel 414. A layer or cover 442 may be deposited on the device 410 according to known techniques covering the membranes 422. One or more reservoirs 410 are located proximate the second end 426 and formed through the cover 442. In this way, the membranes 422 are in communication with channel 414 and reservoir 410. According to some embodiments of the present invention, the membranes 422 are generally perpendicular to the channel 414 and parallel to each other, although the invention is not limited in this respect. Further, the membranes 422 may be evenly spaced from each other along the length of channel 414. However, even spacing between membranes 422 is not a requirement and the membranes 422 may be so spaced to fit the needs of a particular application or fabrication parameters.

Three membranes 422 are shown in FIG. 8. However, the number of membranes 422 in any particular embodiment may depend upon the desired degree of particle focusing. For example, in an application where a higher degree of resolution is required, the device 410 will have more membranes 422 than in an application where less resolution is necessary. Thus, the invention is not limited as to the number of membranes 422. Moreover, the membranes 422 may be engineered for optimal particle focusing. In some embodiments, two or more membranes of differing molecular weight cutoff (MWCO) may be used in a single device. The choice of material depends upon the application for which the device 410 is to be used and/or fabrication parameters.

In some embodiments, a second layer 420 may be formed on top of the substrate 412. The substrate 412 and layer 420 are not required to be the same material in any given embodiment. Reservoirs 430 and 432 may be formed at least through layers 442, 420 into substrate 412 to couple with ends 416 and 418 respectively of channel 414. In this way, the length of the channel 414 at each end 416 and 418 is extended by the diameter or length of the reservoirs 430 and 432. In embodiments that include additional layers, at least a portion of reservoirs 430 and 432 will be formed through the additional layers such that the reservoirs 430 and 432 will not be completely covered, thereby allowing the user of the device 410 to access the reservoirs. As shown in FIG. 8, reservoirs 430 and 432 are generally circular. However, the reservoirs 430 and 432 may be any shape and depth that is suitable for the particular application in which the device 410 is to be used and/or allowed by processing parameters.

The device 410 may undergo additional processing to form various electrodes in association with reservoir 430, channel 414 and/or reservoirs 410. In all embodiments, the electrodes should not obstruct the sort or separation of charged particles. A first electrode 434 may be disposed within reservoir 430. According to some embodiments, the electrode 434 may be a ground or reference electrode adapted to receive either negative or positive voltage when the device 410 is in use. For example, when negatively charged particles are to be classified, electrode 434 will be negatively charged. Alternately, where positively charged particles are to be separated according to embodiments of the present invention, electrode 434 will be positively charged.

Electrodes 436 extend into the channel 414 proximate to the membrane ends 424. Each electrode 436a, 436b and 436c is separated from electrode 434 by a different distance. Moreover, according to embodiments of the present invention, electrodes 436a, 436b and 436c receive a voltage such that the potential difference between electrode 434 and electrodes 436a, 436b and 436c differs. As such, a voltage gradient with respect to reference electrode 434 may be applied to a solution to cause charged particles in the solution to migrate in channel 414.

In some embodiments, the applied voltage gradient may be positive (or negative depending upon the particles to be sorted) and linear, increasing from reservoir 430 toward reservoir 432. However, other voltage or electric field gradients may be produced as well. For example, the electric field gradient may be liner for a period of time and non-linear at a different point in time. Although electrodes 434 and 436 are shown in the figures as being disposed in reservoir 430 proximate the ends 424 of membranes 422 respectively, the positioning (and number) of the electrodes 434 and 436 may be varied according to design preferences and/or experimental needs. In the embodiment shown in FIG. 8, there is a one to one correspondence between the number of membranes 422 and electrodes 436. The scope of the invention however, is not limited in this respect and there may be any number of gradient producing electrodes 436. Advantageously, when at least some of the gradient producing electrodes 436 are proximate to or disposed in membranes 422, particles having similar charge and absolute mobility characteristics will focus and collect therein.

An electrode 440 may be disposed in the reservoir 410, near end 426 of membrane 422. The electrodes 436 may be utilized to form a pair with electrodes 440. The formation of electrodes 434, 436 and 440 and their corresponding leads may be achieved by various fabrication techniques as is known in the art and may be formed in any way that will achieve the desired result both on the micro and macro scale. The electrodes 434, 436 and 440 may receive voltage from any suitable power supply. The power supply may be external or internal. Thus, the scope of the present invention is not to be limited by the manner in which voltage is supplied to the electrodes.

Figure 9:
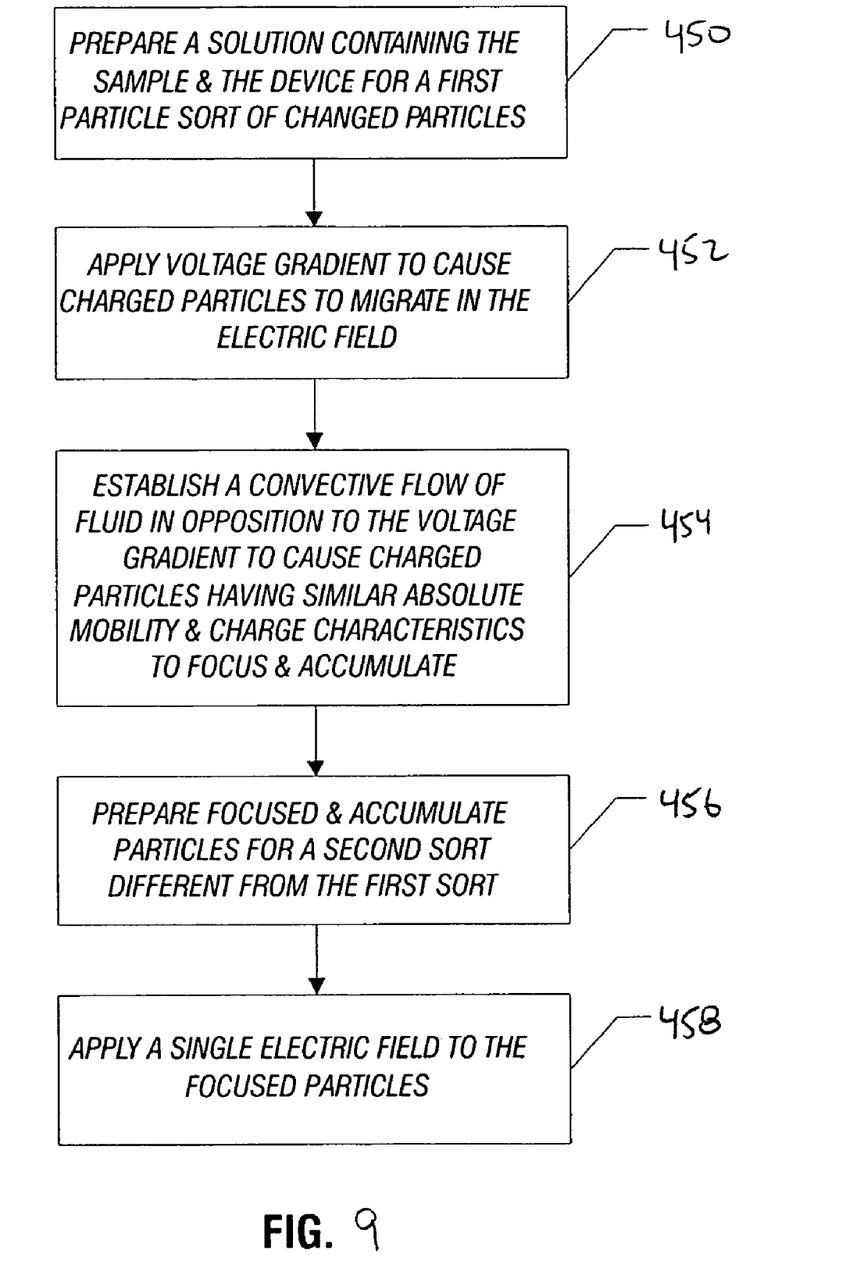
FIG. 9 is a block flow diagram for the separation of particles in two ways according to some embodiments of the invention.

Referring to FIG. 9, prior to device 410 use, a sample may be prepared for loading into reservoir 430 as shown in block 450. Generally, the sample may be suspended in a liquid such as a buffer at a given pH. However, the invention is not so limited and the sample may be prepared in any manner that will achieve the desired particle separation. Where the device 410 is used in biological applications, the sample may be a pre-purified mixture of charged particles such as nucleic acids or proteins, although the invention is not so limited. As described herein for exemplary purposes only, the mixture of particles to be sorted using device 410 are peptides and proteins. However, the device 410 may be used to sort any charged particles, biological, pre-purified or not. Further, a mixture of uncharged molecules that are individually associated with a charged carrier may be separated using device 410. Thus, the type of particles to be separated and characterized using device 410 are not limited.

Channel 414 and reservoirs 430, 432 and 410 may be filled with one or more fluids, as indicated in block 450. The fluid may be the same fluid that the sample is dissolved in, although the invention is not so limited. Accordingly, any number of fluids may used to fill the channel 414 and the reservoirs 430 and 432.

Before, during or after sample loading in reservoir 430, an electric field gradient may be applied to the solution to cause charged proteins/peptides in the sample to migrate in channel 414 as outlined in block 452. For example, the voltage to electrodes 434 and 436a, 436b and 436c may be adjusted until the desired gradient is established. In this example, a positive voltage gradient is generated such that the potential difference between electrodes 434 and 436a is the least and the potential difference between electrodes 434 and 436c is the greatest; the potential difference between electrode 434 and 436b is there between to create a linearly increasing positive voltage gradient in channel 414. As a result, negatively charged proteins and peptides will leave well 430 and migrate through channel 414 toward reservoir 432. In contrast, positively charged and uncharged proteins/peptides will tend to remain in the reservoir 430. However, if positively charged particles are to be separated, the polarity of electrodes 434 and 436 may be reversed to generate a negative electric field gradient thereby causing positively charged particles to migrate in the electric field.

According to some embodiments of the invention, the potential difference between the first electrode 434 and any one of the electrodes 436 may range from about 0.1 volts (V)

to about 300 V. For example, in one embodiment, the potential at electrodes 436a, 436b and 436c may be 2.5 V, 5 V and 10 V respectively.

Likewise, before, during or after sample loading in reservoir 430, a convective fluid flow may be established in channel 414 as indicated in block 454. For example, fluid may be moved from fluid source reservoir 432 toward reservoir 430 through the channel 414. Generally, when charged particles electrophoresed in a voltage gradient are opposed by a convective fluid flow they will sort based on their overall charge and absolute mobility. This technique of particle sorting or separating is typically known as counteractive chromatography. Thus, through the use of counteractive chromatography, and under a given set of conditions, molecules having similar charge and absolute mobility characteristics will stop migrating or focus at a unique position in channel 14 where the forces due to the electric field gradient and convective fluid flow balance or are cancelled out. As a result, one or more bands or groups of similarly focused particles will be distributed along the length of channel 414.

For example, proteins having similar charge that migrate about the same distance in channel 414 in opposition to the calculated convective fluid flow may focus at or near one of the electrodes 436a, 436b or 436c. Thus, according to this example, there will be at least three groups of similarly focused proteins. Increasing the number of electrodes 436 along the length of channel 414 increases the number of focusing and accumulation points, hence the resolution of the system.

The force of convective fluid flow is calculated to enhance focusing of charged molecules. A conventional external pump may establish the convective flow of fluid. Alternately, in some embodiments, the convective flow of fluid may be established by a MEMS pump such as an electroosmotic pump or piezoelectric micropump. However, embodiments of the present invention should not be limited by the means for establishing convective fluid flow whether it is by pump, gravitational pull or other means.

After a desired length of time, counteractive chromatography may be terminated such that the focused particles that have accumulated at or near the end may undergo further separation in the membrane 422. The charged particles may be caused to migrate through the membrane 422, acting as a sieve, thereby sorting the particles in a second direction or dimension as indicated in block 458. For example, when a potential is applied across electrodes 436 and 440, the negatively charged proteins/peptides will be drawn toward the positive electrode. However, the sieve impedes the progress of the charged particles. Thus, the proteins and peptides first sorted in the electric field gradient may be further separated in membranes 422.

After a given amount of time, the electric field between electrodes 436 and 440 may be removed to stop the second separation. The separated particles may be detected by any known means. For example, in some embodiments the charged particles may be stained, or if radioactive, a film may be exposed. Largely, the user of the device 410 decides what technique should be used for particle detection. Thus, the scope of the present invention should not be limited in this respect.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A microfluidic device comprising:
    a unitary body comprising a first fluid passage; a second fluid passage; a membrane positioned separating the first fluid passage from the second fluid passage and in communication with the first fluid passage and the second fluid passage;
    a first electrode positioned in the first fluid passage; and
    a second electrode positioned in the second fluid passage;
    wherein a potential applied to the first and second electrodes passes charged molecules from the first fluid passage to the second fluid passage through the membrane,
    wherein the first fluid passage includes one or more first reservoirs and the first electrode is positioned in one of the first reservoirs, and
    wherein the first fluid passage, the membrane and the second fluid passage form a 3-level structure with the first passage and the second passage separated by the membrane.

2. The device of claim 1, wherein the body is polymethylsiloxane material (PDMS).

3. The device of claim 1, wherein the membrane is a gel made of agarose.

4. The device of claim 1, wherein the membrane is a semipermeable membrane made of regenerated cellulose.

5. The device of claim 1, wherein the second fluid passage includes one or more second reservoirs and the second electrode is positioned in one of the second reservoirs.

6. The device of claim 1, further comprising an elongated membrane passage disposed within the unitary body, the elongated membrane passage positioned between and contacting the first fluid passage and the second fluid passage.

7. The device of claim 6, wherein the first fluid passage, the second fluid passage and the membrane passage are elongated cylindrical passages, wherein an outer diameter of the first fluid passage and an outer diameter of the second fluid passage contact the membrane passage.

8. The device of claim 6, wherein the membrane is a gel plug.

9. The device of claim 6, wherein the unitary body includes an upper surface a lower surface and side surfaces, the elongated membrane passage extending across the unitary body from a first side surface to a second side surface.

10. The device of claim 1, wherein the unitary body including an upper surface a lower surface and side surfaces, the membrane extending across the unitary body from a first side surface to a second side surface.

* * * * *